United States Patent [19]
Ginsberg et al.

[11] Patent Number: 5,932,421
[45] Date of Patent: Aug. 3, 1999

[54] METHODS AND CELL LINES FOR IDENTIFICATION OF REGULATORS OF INTEGRIN ACTIVATION

[75] Inventors: Mark H. Ginsberg, San Diego; Csilla Fenczik, Encinitas, both of Calif.

[73] Assignee: The Scripps Research Institute, La Jolla, Calif.

[21] Appl. No.: 08/948,221

[22] Filed: Oct. 9, 1997

Related U.S. Application Data

[60] Provisional application No. 60/033,248, Dec. 6, 1996.
[51] Int. Cl.$^6$ .............................. C12Q 1/02; C12Q 1/68; C12N 5/10
[52] U.S. Cl. ................................ 435/6; 435/29; 435/325; 435/358
[58] Field of Search .................................. 435/6, 29, 325, 435/358

[56] References Cited

PUBLICATIONS

Akiyama et al., "Transmembrane Signal Transduction by Integrin Cytoplasmic Domains Expressed in Single–subunit Chimeras", 1994 *J. Biol. Chem.* 269:159.

Baker et al., "A genetic analysis of integrin function: Glanzmann thrombasthenia in $^{vitro}$", 1997 *Proc. Nat'l Acad. Sci. USA* 94:1973–1978.

Berditchevski, F. et al., "Characterization of Novel Complexes on the Cell Surface between Integrins and Proteins with 4 Transmembrane Domains (TM4 proteins)", 1996 *Mol. Biol. Cell* 7:193.

Bierhuizen et al., "Expression cloning of a cDNA encoding UDP–GlcNAc:Galβ1–3–GalNAc–R(GlcNAc to GalNAc) β1–6GlcNac transferase by gene transfer into CHO cells expressing polyoma large tumor antigen", 1992 *Proc. Nat'l Acad. Sci. USA* 89:9326–9330.

Chen, Y. et al., "'Inside'–out Signal Transduction Inhibited by Isolated Integrin Cytoplasmic Domains", 1994 *J. Biol. Chem.* 269:18307–18310.

Gaul, U. et al., "Identification of ras targets using a genetic approach", 1994 *Ciba Found. Symp.* 176:85.

Hannigan, G.E. et al., "Regulation of cell adhesion and anchorage–dependent growth by a new β$^1$–integrin–linked protein kinase", 1996 *Nature* 379:91–95.

Hirt et al., "Selective Extraction of Polyoma DNA from Infected Mouse Cell Cultrues", 1967 *J. Mol. Biol.* 26:365–369.

Horwitz et al., Interaction of plasma membrane fibronectin receptor with talin–a transmembrane linkage, 1986 *Nature* 320:531.

Hughes, P. et al., "Suppression of Integrin Activation: A Novel Function of a Ras/Raf–Initiated MAP Kinase Pathway", 1997 *Cell* 88:521.

Hynes, R.O., "Integrins: Versatility, Modulation, and Signaling in Cell Adhesion", 1992 *Cell* 69:11–25).

Kolanus, W. et al., "αLβ2 Integrin/LFA–1 Binding to ICAM–1 Induced by Cytohesin–1, a Cytoplasmic Regulatory Molecule", *Cell* 86:233–242.

LaFlamme et al., "Regulation of Fibronectin Receptor Distribution", 1992 *J. Cell Biol.* 117:437–447.

LaFlamme et al., "Single Subunit Chimeric Integrins as Mimics and Inhibitors of Endogenous Integrin Functions in Receptor Localization, Cell Spreading and Migration, and Matrix Assembly", 1994 *J. Cell Biol.* 126:1287–1298.

Lindberg, F.P. et al., "Molecular Cloning of Integrin–associated Protein: An Immunoglobulin Family Member with Multiple Membrane–spanning Domains Implicated in $α^vβ^3$–dependent Ligand Binding", 1993 *J. Cell Biol.* 123:485.

Lukashev, M.E. et al., "Disruption of Integrin Function and Induction of Tyrosine Phosphorylation by the Autonomously Expressed β$^1$ Integrin Cytoplasmic Domain", 1994 *J. Biol. Chem.* 269:18311–18314.

Otey et al., "An Interaction between α–Actinin and the β$^1$ Integrin Subunit In Vitro", 1990 *J. Cell. Biol.* 111:721.

Quackenbush et al., "Molecular cloning of complementary DNAs encoding the heavy chain of the human 4F2 cell–surface antigen: A type II membrane glycoprotein involved in normal and neoplastic cell growth", 1987 *Proc. Natl. Acad. Sci. USA* 84:6526–6530.

Rojiani et al., "In Vitro Interaction of a Polypeptide Homologous to Human Ro/SS–A Antigen (Calreticulin) with a Highly Conserved Amino Acid Sequence in the Cytoplasmic Domain of Integrin α Subunits", 1991 *Biochem.* 30:9859.

Schwartz, M.A. et al., "Integrins: Emerging Paradigms of Signal Transduction", 1995 *Ann. Rev. Cell Dev. Biol.* 11:549–599.

Shattil, S.J. et al., "β$^3$–Endonexin, a Novel Polypeptide That Interacts Specifically with the Cytoplasmic Tail of the Integrin β$^3$ Subunit", 1995 *J. Cell. Biol.* 131:807–816.

Shattil et al., "Changes in the Platelet Membrane Glycoprotein IIb IIIa Complex during Platelet Activation", 1985 *J. Biol. Chem.* 260:11107.

Therrien, M. et al., "KSR, a Novel Protein Kinase Required for RAS Signal Transduction", 1995 *Cell* 83:879.

Wei, Y. et al., Regulation of Integrin Function by the Urokinase Receptor, 1996 *Science* 273:1551.

White et al., "Multiple Ras Functions Can Contribute to Mammalian Cell Transformation", 1995 *Cell* 80:533–541.

*Primary Examiner*—Johnny F. Railey, II
*Attorney, Agent, or Firm*—Law Offices of Jane Massey Licata

[57] ABSTRACT

A method for identifying regulators of integrin activation by establishing a selected cell line which contains a functional integrin and a chimeric polypeptide having a cytoplasmic domain of an integrin subunit fused to a polypeptide containing extracellular and transmembrane domains that are not functional integrin domains, so that chimera can inhibit signaling activities of the functional integrin by interaction with integrin regulator molecules in the cytoplasm; transfecting the cell line with a selected cDNA expression library; expressing proteins of the cDNA expression library; and identifying proteins which when overexpressed overcome the inhibition of signaling activities by said chimeric polypeptide, said proteins being regulators of integrin. Methods of designing drugs to modify integrin function and cell lines for screening regulators of integrin activation are also provided.

4 Claims, No Drawings

METHODS AND CELL LINES FOR IDENTIFICATION OF REGULATORS OF INTEGRIN ACTIVATION

This application claims the benefit of U.S. Provisional Application No. 60/033,248, filed Dec. 6, 1996.

INTRODUCTION

This invention was made with government support under Contract No. HL48728 by the NIH. The government has certain rights in the invention.

FIELD OF THE INVENTION

The invention relates to methods for cloning regulators of integrin function, and more particularly to screening methods using expression libraries to clone and identify regulators which act via integrin cytoplasmic domains.

BACKGROUND OF THE INVENTION

Integrins are a class of widely distributed cell surface adhesion receptor membrane proteins that are essential for normal vertebrate development. These proteins play a key role in a variety of physiological processes including thrombosis, inflammation, restenosis, and malignant transformation (Schwartz, M. A. et al. 1995 *Ann. Rev. Cell Dev. Biol.* 11:549–599; Hynes, R. O. 1992 *Cell* 69:11–25). Accordingly, modulation or regulation of integrin function has been proposed as a strategy for development of numerous therapeutics (Schwartz, M. A. et al. 1995 *Ann. Rev. Cell Dev. Biol.* 11:549–599; Hynes, R. O. 1992 *Cell* 69:11–25).

Integrin proteins are heterodimeric and consist of two polypeptide subunits, $\alpha$ and $\beta$, that pair to form more than 20 distinct receptors (e.g., $\alpha IIb/\beta 3$, $\alpha 1/\beta 1$, $\alpha 2/\beta 1$, etc.; Hynes, R. O. 1992 *Cell* 69:11–25). These receptors generally consist of a large extracellular domain formed by the $\alpha$ and $\beta$ subunits, a transmembrane segment also from Each subunit, and two short cytoplasmic C-terminal tails (Schwartz, M. A. et al. 1995 *Ann. Rev. Cell Dev. Biol.* 11:549–599). The extracellular domains bind to proteins or other receptors in the extracellular matrix while the cytoplasmic domain forms a link to the cytoplasmic skeleton.

These receptor proteins can transmit information in both directions across the plasma membrane. As a result, integrins may transduce signals within cells to initiate cellular processes such as division, secretion, or gene expression. An important feature of these proteins is that they often must undergo activation in order to initiate cellular activity (Hynes, R. O. et al. 1992 *Cell* 69:11–25). Stimuli for activation may include soluble mediators such as hormones and cytokines as well as solid-phase reactants such as the extracellular matrix of another cell. Integrins are activated at the appropriate time and place in the cell through input by specific physiological signals such as thrombogenic agonists, antigen, cytokines, or T cells (Hynes, R. O. et al. 1992 *Cell* 69:11–25). Similarly, inactivation of integrins is also important to maintenance of homeostasis in mammalian systems.

Methods for identifying binding partners of integrin function include the yeast two hybrid cloning system and affinity chromatography (Shattil, S. J. et al. 1995 *J. Cell. Biol.* 131:807–816; Hannigan, G. E. et al. 1996 *Nature* 379:91–95; Kolanus, W. et al. *Cell* 86:233–242). However, there is a need for methods and systems for identifying regulators which activate integrins in mammalian cells.

SUMMARY OF THE INVENTION

An object of the present invention is to provide a method of identifying regulators of integrin activation which comprises establishing a selected cell line containing a functional integrin; introducing into the selected cell line a chimeric polypeptide leaving the cytoplasmic domain of an integrin subunit fused to a polypeptide containing extracellular and transmembrane domains that are not functional integrin domains so that the chimera can inhibit signaling activities of the functional integrin by interaction with integrin regulator molecules in the cytoplasm; transfecting the selected cell line with a selected cDNA expression library; expressing proteins of the selected cDNA expression library; and identifying proteins which, when overexpressed, overcome the inhibition of signaling activities by said chimeric polypeptide, said proteins being regulators of integrin activation.

Another object of the present invention is to provide a cell line for screening for regulators of integrin activation which comprises a functional integrin; a chimeric polypeptide having a cytoplasmic domain of an integrin subunit fused to a polypeptide containing extracellular and transmembrane domains that are not functional integrin domains so that the chimeric polypeptide can inhibit signaling activities of said functional integrin; and selected cDNA expression library which expresses proteins in the cell line which are identified as regulators by integrin activation by their overexpression overcoming the inhibition of signaling activities of the functional integrin by the chimeric polypeptide.

Another object of the present invention is to provide a method of identifying targets for designing therapeutic agents which modify integrin activation.

DETAILED DESCRIPTION OF THE INVENTION

Integrins are adhesion receptors that regulate cell growth and migration and participate in development, hemostasis, inflammation and the immune response. Integrin $\alpha$ and $\beta$ subunits each contain a large extracellular domain, a single transmembrane segments and cytoplasmic domain. The ligand binding affinity of integrins changes in response to intracellular signals, referred to herein as activation. Conversely, occupancy of integrins controls shape, growth, survival and programs of gene expression. Integrin signaling is mediated via specific amino acid sequences in the cytoplasmic domain of both subunits. Proteins that interact with integrin cytoplasmic domains have been identified (Hannigan et al. 1996 *Nature* 379:91; Kolanus Et al. 1996 *Cell* 86:233; Otey et al. 1990 *J. Cell. Biol.* 111:721; Horwitz et al. 1986 *Nature* 320:531; Rojiani et al. 1991 *Biochem.* 30:9859; and Shattil et al. 1995 *J. Cell Biol.* 1231:807), however the role of these interactions in integrin signaling is still uncertain.

Genetic strategies have been demonstrated to be useful in analyzing intracellular signal transduction pathways. For example, one such strategy seeks suppressors or enhancers of the effects of activated or dominant negative mutants of signaling molecules (Gaul, U. et al. 1994 *Ciba Found. Symp.* 176:85; Therrien, M. et al. 1995 *Cell* 83:879).

Overexpression of isolated integrin $\beta 1$ cytoplasmic domains in the form of chimeras with the Tac subunit of the IL-2 receptor (Tac-$\beta 1$), interferes with bidirectional integrin signaling, referred to herein as dominant suppression (Chen et al. 1994 *J. Biol. Chem.* 269:18307; Akiyama et al. 1994 *J. Diol. Chem.* 269:159; and Lukashev et al. 1994 *J. Biol. Chem.* 269:18311). In the present invention, a genetic strategy has been developed to isolate proteins involved in integrin signaling by their capacity to complement dominant suppression. Using this strategy, the present invention provides a method of screening for regulators which activate integrin function which relies upon a novel approach to cloning cDNAs encoding regulators of integrin activation by complementation of the dominant negative effects of a free integrin tail. CD98, an early T cell activation antigen, was identified, through methods of the present invention, as a regulator of integrin function. Further, it was determined that the activity of this protein resides in the cytoplasmic tail of CD98, a small region susceptible to small molecule inhibition. Accordingly, the method of the present invention is believed to be useful in identifying potential targets for the design of therapeutic agents which modulate integrin function.

In the method of the present invention a selected cell line is established which contains a functional integrin. By "functional integrin" it is meant an integrin subunit capable of interacting with intracellular components and transmitting detectable information. This functional integrin can be introduced into the selected cell line by transfection or may be endogenous to the selected cell line. Cells of the cell line are then transfected with a chimeric polypeptide having the cytoplasmic domain of an integrin subunit fused to a polypeptide containing extracellular and transmembrane domains that are not functional integrin domains, so that the chimera can inhibit signaling activities of the functional integrin by interaction with integrin regulator molecules in the cytoplasm. The functional integrin and the chimera can each be introduced to the cell by a variety of means well known to those of skill in the art, including but not limited to, by endogenous expression, by a transgene in the cell, or by transient expression of an expression vector. A selected cDNA expression library is then introduced and expressed in the cell line. Any integrin regulators expressed by the library will bind integrin cytoplasmic domains. Overexpression of the integrin regulators will overcome the inhibition by the chimera, and signaling will occur, thus indicating expression of a functional regulator.

In one embodiment the cell line used in this method expresses a chimeric integrin containing the extracellular and transmembrane domains of $\alpha_{IIb}\beta_3$ and the cytoplasmic domains of $\alpha_6 A\beta_1$. It is preferred, at least for this chimeric integrin, that Chinese Hamster Ovary (CHO) cells be used as this chimeric integrin is constitutively active when expressed in CHO cells as determined by the binding of the monoclonal antibody PAC1, which is specific for the high affinity form of $\alpha_{IIb}\beta_3$ (Shattil et al. 1985 *J. Biol. Chem.* 260:11107). Expression of isolated $\beta 1$ tails in the form of Tac-$\beta 1$ chimera in these cells results in the cell autonomous suppression of integrin activation in the cells, as manifested by reduced PAC1 binding in the cells that express Tac-$\beta 1$.

Proteins that complement trans-dominant suppression in cells expressing the chimeric integrin containing the extracellular and transmembrane domains of $\alpha_{IIb}\beta_3$ and the cytoplasmic domains of $\alpha_6 A\beta_1$ were identified by co-transfecting the cells with a CHO cell cDNA library directionally cloned into the pcDNA1 expression vector. Cells binding high levels of both anti-Tac and PAC1 antibodies were isolated by fluorescence activated cell sorting (FACS). cDNAs enriched for complementing activity were then isolated from these sorted cell populations.

Six such experiments resulted in the isolation of 1200 cDNAs which were then grouped into 75 pools of 16 cDNAs each. One out of 75 pools contained cDNA that complemented trans-dominant suppression. This pool was divided into four groups of four cDNAs, only one of which was active. In this smaller pool, only a single cDNA, 5F8, reversed trans-dominant suppression.

The CHO cell cDNA library was further screened in four additional experiments which resulted in the enrichment of 1059 more cDNA clones. Three additional cDNAs identical to clone 5F8 were isolated among these experiments. Consequently, in this cDNA library, 5F8 seems unique in complementing trans-dominant suppression. The CHO cell cDNA library has a high complexity with a relatively large number of independent clones. Thus, the effect of 5F8 appears to be highly specific.

To further confirm the specificity of this effect, the ability of expression plasmids encoding proteins reported to interact with integrin cytoplasmic domains to overcome trans-dominant suppression was tested. Transfection of cDNAs encoding α-actinin, vinculin, paxillin, and $\beta 3$ endonexin had no effect on the capacity of Tac-$\beta 1$ to block integrin activation.

The cytoplasmic domain specificity of the effect of 5F8 was also examined. Specifically, the ability of 5F8 to complement suppression initiated by a $\beta 1$ tail and transmembrane domain joined to the extracellular domain of CD4 was assessed. As with Tac-$\beta 1$, co-transfection of 5F8 with CD4/$\beta 1$ resulted in a reversal of dominant suppression, indicating that the rescue was independent of the extracellular domain of the suppressive chimera. The isolated $\beta 3$ cytoplasmic domain has been shown by others to be able to initiate trans-dominant suppression as well (Chen et al. 1994 *J. Biol. Chem.* 269:18307; LaFlamme et al. 1994 *J. Cell Biol.* 126:1287–1298). 5F8 reversed Tac-$\beta 3$ suppression as well. Thus, 5F8 can complement suppression initiated by either $\beta 1$ or $\beta 3$ cytoplasmic domains.

To determine whether 5F8 was increasing the activation of the chimeric integrin as well as reversing trans-dominant inhibition, 5F8 was co-transfected with Tac-$\alpha 5$ into the CHO cell line that expresses the chimeric integrin. The level of integrin activation in cells expressing 5F8 and Tac-$\alpha 5$ was identical to the activation level in control cells. These results evidence that the increase of integrin activation that is seen when clone 5F8 is over expressed is a recovery from Tac-$\beta 1$ suppression.

The product encoded by 5F8 was then determined. The 5F8 insert contains 1902 base pairs, containing an open reading frame encoding a 533 amino acid polypeptide. In addition, it contains a polyA tract and polyadenylation signal. Analysis of the predicted topology of the encoded protein indicated that it possesses a single transmembrane domain with the N terminus inside the cell (Type II transmembrane protein). A BLAST database search showed that 5F8 is related to the heavy chain of the 4F2 antigen, CD98, from both mouse and human. The predicted hamster sequence is 72% identical to the human protein and thus appears to be the hamster homologue of CD98.

Accordingly, experiments were performed to determine whether human CD98 could substitute for the hamster protein in reversing trans-dominant inhibition. In these experiments, the cDNA for human CD98 was co-transfected with Tac-$\beta 1$. Results showed that overexpression of human CD98 complemented dominant suppression.

Since CD98 is a transmembrane protein, the method of the present invention was used to screen other membrane proteins for the ability to reverse trans-dominant suppression. Experiments were performed wherein membrane proteins that had previously been implicated in integrin function were overexpressed: CD9 (Berditchevsli, F. et al. 1996 *Mol. Biol. Cell* 7:193), CD47 (IAP; Lindberg, F. P. et al. 1993 *J. Cell Biol.* 123:485), and urokinase plasminogen activator receptor (UPAR; Wei, Y. et al. 1996 *Science* 273:1551).

However, expression of these proteins failed to reverse the dominant suppression by Tac-β1. Protein expression was confirmed by flow cytometry in each case. Thus, the Tac-β1 suppression resulting from over expression of CD98 is a specific effect which does not result from the over expression of membrane proteins in general.

To determine whether CD98 promoted the activation of the chimeric integrin as well as reversing dominant suppression, cDNAs encoding CD98 and the other membrane-associated proteins were co-transfected in the absence of Tac-β1. None of these proteins altered the level of activation. Furthermore, over expression of CD98 failed to activate recombinant αIIb/β3. These data show that CD98 reversal of dominant suppression is due to the complementation of the negative effects of Tac-β1 rather than a general increase in integrin activation.

It has been shown by others that a Ras-initiated MAP kinase pathway suppresses integrin activation (Hughes, P. et al. 1997 *Cell* 88:521). Therefore, experiments were performed to determine whether CD98 could complement this effect. Transfection of an activated Ras (G12V) inhibited PAC1 binding. The degree of inhibition was not affected by expression of CD98. In contrast, expression cf MAP kinase phosphatase (MKP-1) reduced Ras suppression. CD98 was functional since, in simultaneous assays, it complemented Tac-β1 suppression. These data demonstrate that CD98 does not complement all inhibitors of integrin activation.

Experiments were also performed to determine whether the Tac-β1 suppressive effect was dependent on the Ras-initiated MAP kinase pathway. Expression of Tac-β1 did not activate ERK-2 MAP kinase, while ERK-2 was activated by the expression of an activated H-Ras. Furthermore, co-transfection of MKP-1 failed to reverse the suppressive effect of Tac-β1, whereas co-expression of CD98 overcame this effect. These results indicate that the mechanisms of suppression of integrin activation by Ras, or by expression of isolated β1 tails, differ.

The experiments with CD98 identify this protein for the first time as an integrin regulatory protein through use of the system of the present invention. Data show that CD98 complements trans-dominant inhibition of integrin activation by isolated integrin cytoplasmic domains. Complementation of trans-dominant suppression by CD98 is highly specific, as shown by results in experiments where transfection with several other cytoplasmic and membrane proteins failed to complement its activity. The CD98 complementation is independent of the extracellular domain of the chimera and can complement suppression initiated by either the β1 or β3 tail. Further, data show that CD98 does not complement the integrin suppressive pathways initiated by the activated Ras oncogene.

In similar fashion to the identification of CD98 as an integrin regulator, those of skill in the art can routinely use the method of the present invention to identify other integrin regulators. Further, the methods can be practiced with any of the integrins and is not limited to the integrins exemplified in this specification. Any extracellular and transmembrane polypeptide domains can be used in the chimera, so long as the chimera can inhibit normal signaling.

The method of the present invention is thus useful in designing drugs to modify integrin function which are targeted to either the molecules or portions of molecules identified by the method of the present invention or to a region of the integrin to which the molecules bind. Once a molecule or portion of a molecule is identified as a regulator or activator, drugs predicted based upon their molecular structure to interact with the identified molecule or a region of integrin to which the identified molecule binds can be designed. For example, using the method of the present invention it was found that CD98, and more particularly, the cytoplasmic tail of CD98 regulates integrin function. Accordingly, drugs targeted to this region of the CD98 protein may be useful in modifying integrin function. Alternatively, drugs targeted to the region oat integrin to which the CD98 protein binds may also be useful in modifying integrin function. Similarly, drugs targeted to other molecules identified as regulators of integrin function by the method of the present invention or a region of the integrin to which they bind which will be useful in modifying integrin function can also be designed.

The following non-limiting examples are provided to further describe the present invention

EXAMPLES

Example 1

Antibodies and Reagents

The anti-β3 monoclonal antibody was antibody LIBS6. The activation specific anti-αIIb/β3 monoclonal antibody was PAC1. The anti-Tac antibody, 7G7B6, was obtained from the American Type Culture Collection (Rockville, Md.). The anti-Tac antibody was biotinylated with biotin-N-hydroxy-succinimide according to the manufacturer's directions (Sigma Chemical Co., St. Louis, Mo.). The αIIb/β3-specific peptidomimetic inhibitor was Ro43–5054.

Example 2

Preparation of CDNA Constructs and Transfection Experiments

The Tac-β1 and α5 chimeras used in the CMV-ILR2 vector were described by LaFlamme et al. 1992 *J. Cell Biol.* 117:437–447. Tac-β3 has also been described previously by LaFlamme et al. 1994 *J. Cell Biol.* 126:1287–1298. Expression plasmids of both L3T4/β1 chimeras were comprised of Ch1, which contains the extracellular domain of murine CD4 fused to the β1 transmembrane and cytoplasmic domains, and Ch2, which lacks the β1 cytoplasmic domain as described by Lukashev, M. E. et al. 1994 *J. Biol. Chem.* 269:18311–18314. The vector expressing MKP-1, pSG5 MKP-1, was described previously by Sun et al. 1993 *Cell* 75:487–493. The plasmid pDCR-H-Ras (G12V) was described previously by White et al. 1995 *Cell* 80:533–541. The human 4F2 antigen cDNA subcloned into puc13 has been described by Quackenbush et al. 1987 *Proc. Natl. Acad. Sci. USA* 84:6526–6530. Expression construct encoding CD9 and uPAR, pcuPAR1, were also used along with the plasmid, pIAP45, which expresses CD47.

Chinese Hamster Ovary (CHO-K1) cells were obtained from the American Type Culture Collection (Manassas, Va.). These cells were stably transfected with pPSVE-PyE, which encodes the polyoma large T antigen and replication deficient CDM8 expression constructs encoding αIIb/α6a and β3/β1 in accordance with procedures described by Baker et al. 1997 *Proc. Nat'l Acad. Sci. USA* 94:1973–1978. All cell lines were grown in Dulbecco's modified Eagle's medium (DMEM; BioWhittaker, Walkersville, Md.) containing 10% fetal bovine serum, 1% non-essential amino acids, 2 mM glutamine and 100 units per milliliter of penicillin and 100 micrograms per milliliter of streptomycin.

Cells were transfected using a lipofectamine procedure. For each 10 cm tissue culture dish with 40–60% confluent cells, 20 μl of lipofectamine reagent (GibCo BRL, Gaithersburg, Md.) and 10 μg of plasmid DNA were mixed in 200 μl of DMEM. After 10 minutes of incubation, the DNA-lipofectamine mixture was diluted 1:20 and added to the cells. The cells were incubated for 6 hours and then washed with complete medium. Cells were incubated for 48 hours at 37° C.

Example 3

Flow Cytometry

PAC1 binding was analyzed by two-color flow cytometry as described by Chen, Y. et al. 1994 *J. Biol. Chem.* 269:18307–18310. Transfected cells were detached with cell dissociation buffer (GibCo BRL, Gaithersburg, Md.) for 5 minutes at room temperature. The detached cells were pooled, centrifuged, and resuspended in complete medium containing 0.1% of PAC1 ascites. Control cells were also incubated with either 1 μM of the competitive inhibitor, Ro-43-5054, as a negative control, or with anti-LIBS6, an activating antibody, as a positive control. After 30 minutes of incubation at room temperature, the cells were washed and then resuspended in complete medium containing a 1:25 dilution of the biotinylated anti-Tac antibody. 7G7B6. After 30 minutes on ice, the cells were washed and incubated with 10% FITC-conjugated goat anti-mouse IgM and 4% phycoerythrin-streptovidin (Molecular Probes, Inc. Eugene, Oreg.). Thirty minutes later cells were resuspended in phosphate buffered saline (PBS) for flow cytometric analysis.

Example 4

Expression Cloning

A cDNA library, made from polyA(+) mRNA from CHO-K1 cells (Invitrogen, San Diego, Calif.) was directionally cloned into the mammalian expression vector, pcDNA1. The library is reported to contain $1.8 \times 10^7$ primary recombinants and has been amplified once. Plasmid DNA (4 μg/plate) was transfected into the α/β-Py cell line, along with the Tac-β1 chimera (4 μg/plate) using lipofectin as described in Example 2. The transfection efficiency ranged from 30–50%, as judged by 7G7B6 binding.

After a 48 hour incubation, cells were stained for PAC1 and 7G7B6 binding. Cells positive for both PAC1 and 7G7B6 were isolated by fluorescence activated ell sorting (FACSTAR, Becton Dickinson). Gates were set by comparing cells transfected with Tac-α5 with those transfected with Tac-β1 only. Plasmid DNA was extracted as described by Hirt et al. 1967 *J. Mol. Biol.* 26:365–369; digested with Dpn I to remove plasmids that were not replicated in transfected cells; and transformed into the host *E. Coli* MC1061/P3 as described by Bierhuizen et al. 1992 *Proc. Nat'l Acad. Sci. USA* 89:9326–9330. Individual colonies were grown, the bacteria were then pooled into groups of 16 per plasmid purification. Groups of cDNAs were transfected into the α/βPy cell line along with Tac-β1 and the transfectants were screened by flow cytometry as described Example 3. Pools containing cDNAs that altered PAC1 binding were further screened in smaller pools of four, and then the positive pools were screened as individual colonies.

Example 5

DNA Sequencing

The nucleotide sequences were determined with an ABI automated sequencer by using oligonucleotides synthesized according to the flanking sequences and obtained sequences within the insert. Sequences were aligned for comparison using the Sequencer computer program. The entire length of 5F8 was sequenced in both directions.

Example 6

Measurement of ERK2 Activity

For ERK2 assays, $2 \times 10^5$ cells were transfected using methods described in Example 2 with 2 μg of pCMV5 HA-ERK2 (HA; hemagglutinin tagged). The cells were also transfected with 2 μg of test plasmid, e.g., pDCR H-Ras (G12V). In some experiments 4 to 6 μg of a second plasmid (such as MKP-1) were co-transfected and the total amount of DNA was standardized at 10 μg, by the addition of pCDNA1, for each transfection. Transfections were done in duplicate to allow parallel analysis of both ERK2 kinase activity and PAC1 binding by flow cytometry, as described in Example 4. Forty-eight hours post transfection, cells were harvested and lysed in 0.5% NP40 buffer containing phosphatase inhibitors (20 mM NaPyrophosphate and 1 mM $Na_3VO_4$) in addition to protease inhibitors. The activity of the HA-ERK2 was measured by the immune complex in-gel kinase assay method using the anti-HA antibody 12CA5 (Boehringer Mannheim, Indianapolis, Ind.). ERK2 expression was monitored by running 25 μg of whole cell lysate in SDS sample buffer on 12.5% SDS-polyacrylamide gels, transferring to Immobilin, and immunoblotting with anti-HA antibody. Samples were then subjected to SDS-PAGE on 12.5% gels containing 0.5 mg/ml myelin basic protein. The gels were dried down and ERK activity was visually assessed by autoradiography.

What is claimed is:

1. A method for screening for regulators of integrin activation comprising:
   (a) establishing a selected cell line containing a functional integrin;
   (b) introducing into cells of the selected cell line a nucleic acid encoding a chimeric integrin having a cytoplasmic domain of an integrin subunit fused to a polypeptide containing extracellular and transmembrane domains that are not functional integrin domains so that said chimeric integrin inhibits signaling activities of said functional integrin;
   (c) transfecting the cells of (b) with plasmids which comprise a selected cDNA expression library derived from the selected cell line;
   (d) culturing the transfected cells of (c) to express proteins of the selected cDNA expression library;
   (e) identifying individual transfected cells of (d) which contain a plasmid that overexpresses a protein of the selected cDNA expression library, wherein the protein overcomes inhibition of signaling activities by said chimeric integrin; and
   (f) isolating the cells identified in (e) and determining the nucleotide sequence of the cDNA of the plasmid, wherein that the cDNA encodes a protein which is a regulator of integrin activation.

2. The method of claim 1 wherein the selected cell line is the Chinese Hamster Ovary CHO-K1 cell line.

3. The method of claim 2 wherein the functional integrin is the β-1 or β-3 integrin subunit.

4. A cell line for screening for regulators of integrin activation, said cell line made by the method comprising:
   (a) establishing a selected cell line containing a functional integrin;

(b) introducing into cells of the selected cell line a nucleic acid encoding a chimeric integrin having a cytoplasmic domain of an integrin subunit fused to a polypeptide containing extracellular and transmembrane domains that are not functional integrin domains so that said chimeric integrin inhibits signaling activities of said functional integrin; and (c) transfecting the cells of (b) with plasmids which comprise a selected cDNA expression library derived from the selected cell line, wherein the cDNA comprises nucleotide sequences which encode a protein capable of being overexpressed within the transfected cells, said protein overcoming the inhibition of the signaling activities of the functional integrin by the chimeric integrin and thereby identifying said protein as a regulator of integrin activation.

* * * * *

UNITED STATES PATENT AND TRADEMARK OFFICE
CERTIFICATE OF CORRECTION

PATENT NO. : 5,932,421
DATED : August 3, 1999
INVENTOR(S) : Ginsberg et al.

It is certified that error appears in the above-indentified patent and that said Letters Patent is hereby corrected as shown below:

On title page,
In the Publications, under Baker et al., please delete "thrombasthenia in $^{vitro}$" " and insert therefor --thrombasthenia in vitro"--.

In the Publications, under Hirt et al., please delete "Cultrues" and insert therefor --Cultures--.

At col 2, line 3, please delete "leaving" and insert therefor --having--.

At col 2, line 63, please delete "J. Diol." and insert therefor --J. Biol.--.

At col 4, line 35, please delete "5F8 arid Tac" and insert therefor --5F8 and Tac---.

UNITED STATES PATENT AND TRADEMARK OFFICE
CERTIFICATE OF CORRECTION

PATENT NO. : 5,932,421  
DATED : August 3, 1999  
INVENTOR(S) : Ginsberg et al.

Page 2 of 3

It is certified that error appears in the above-indentified patent and that said Letters Patent is hereby corrected as shown below:

At col 4, line 64, please delete "Berditchevsli" and insert therefor --Berditchevski--.

At col 4, line 67, please delete "UPAR" and insert therefor --uPAR--.

At col 5, line 23, please delete "expression cf MAP" and insert therefor --expression of MAP--.

At col 5, line 42, please delete "integrin cytoplasmic" and insert therefor --integrin β cytoplasmic--.

At col 6, line 8, please delete "region oat integrin" and insert therefor --region of integrin--.

At col 6, line 16, please insert therefor --.-- after the word invention.

UNITED STATES PATENT AND TRADEMARK OFFICE
CERTIFICATE OF CORRECTION

PATENT NO. : 5,932,421
DATED : August 3, 1999
INVENTOR(S) : Ginsberg et al.

It is certified that error appears in the above-identified patent and that said Letters Patent is hereby corrected as shown below:

Col. 7, line 45, please delete "activated ell sorting" and insert therefor --activated cell sorting--.

Signed and Sealed this

Twenty-second Day of February, 2000

Attest:

Q. TODD DICKINSON

Attesting Officer

Commissioner of Patents and Trademarks